United States Patent [19]
Hoath et al.

[11] Patent Number: 5,989,577
[45] Date of Patent: Nov. 23, 1999

[54] NONTOXIC VERNIX COMPOSITIONS AND METHOD OF PRODUCING

[75] Inventors: Steven B. Hoath; William L. Pickens; Martha O. Visscher, all of Cincinnati, Ohio

[73] Assignee: Children's Hospital Medical Center, Cincinnati, Ohio

[21] Appl. No.: 09/033,209

[22] Filed: Mar. 2, 1998

[51] Int. Cl.⁶ .................................................. A01N 25/34
[52] U.S. Cl. ........................... 424/402; 424/59; 424/401; 424/443; 424/444; 424/445
[58] Field of Search .................... 424/401, 402, 424/59, 70.1, 443, 445, 444

[56] References Cited

U.S. PATENT DOCUMENTS 5,631,012  5/1997  Shanni .................................... 424/401
5,871,763  2/1999  Luu et al. ............................... 424/402

Primary Examiner—Jose' G. Dees
Assistant Examiner—Kathryne E. Shelborne
Attorney, Agent, or Firm—Wood, Herron & Evans L.L.P.

[57] ABSTRACT

A composition consisting essentially of vernix for a skin curative and skin protectant effect and a method of producing. A natural or synthetic vernix is dispersed in a film-forming amount in a biocompatable liquid such as dimethylsulfoxide, amniotic fluid and/or pulmonary surfactant to form a film. The film may be applied to a growing layer of epithelial cells either directly or supported on a substrate such as a wound dressing, a diaper, or a feminine hygiene product.

51 Claims, No Drawings

NONTOXIC VERNIX COMPOSITIONS AND METHOD OF PRODUCING

The U.S. Government has a paid-up license in this invention and the right in limited circumstances to require the patent owner to license others on reasonable terms as provided for by the terms of Grant No. 5 R01 NR 03699-05 awarded by the National Institutes of Health.

FIELD OF THE INVENTION

The invention relates generally to a therapeutic or prophylactic vernix film for enhanced skin growth and maturation.

BACKGROUND OF THE INVENTION

Skin is one of the largest organs in the body and covers substantially the entire body surface. Skin is composed of two main layers: the surface epithelium or epidermis which includes the uppermost stratum corneum, and the subjacent connective tissue layer or dermis. The skin has a number of functions such as protecting an organism from injury and dessication, receiving environmental stimuli, excreting various substances, regulating body temperature and helping to maintain water balance. Because of its quantitative and qualitative importance, substantially intact and healthy skin is crucial not only for the well being of an organism but for its very survival.

The health and integrity of skin may be compromised by wounds, abrasions, ulcers, burns, infections, irritations, premature birth and other conditions for which normal skin production and repair processes may be inadequate. For example, acute conditions such as patients who are burned over a large surface area often require immediate skin replacement. Less life-threatening but chronic skin problems such as decubitus ulcers or irritations from diaper rash may progress to more severe conditions if left untreated or if they occur in a neonate or a geriatric patient. Skin treatments encompass a variety of methods and products. These may range from symptomatic treatments such as the use of topical anti-inflammatory compounds to the use of replacement skin. For various physiological, medical, and other reasons, however, none of these treatments meet the desired goal of utilizing the body's own healing and repair system to promote its own skin growth and maturation.

Vernix caseosa (vernix) is a naturally occurring skin protectant. Vernix is a lipid rich substance composed of sebum, epidermal lipids, and desquamated epithelial cells that covers the skin of the developing fetus in utero while the fetus is completely surrounded by amniotic fluid. Vernix consists of hydrated cells dispersed in a lipid matrix. This lipid matrix undergoes a transition to a more fluid form at physiological temperatures and with the application of shear forces, such as those encountered with movement. Vernix is a covering for the skin of the fetus that resembles the stratum corneum except that it lacks multiple rigid desmosomal connections. Consequently, vernix exhibits a viscous fluid character.

The lipid component of vernix has been reported in Stewart et al., *J. Invest. Dermatol*, 78:291–295 (1982); Nicolaides, *Lipids* 6:901–905 (1972); Haahti et al., *J. Clin. & Lab. Investigation*, 13:70–73 (1961); Karkkainen et al.,*J. Invest. Dermatol*, 44:333–338 (1965); and U.S. Pat. No. 5,631,012, each of which are incorporated by reference herein in their entirety. Lipids, defined herein as fats or fat-like substances, include lecithin and other phospholipids, squalene, waxes, wax esters, sterol esters, diol esters, triglycerides, free sterols and four classes of fatty acids ranging in chain length from $C_{12}$ to $C_{26}$ (straight chain saturated, straight chain unsaturated, branched chain saturated, and branched chain unsaturated).

Because of its anticipated skin maturation and protectant properties, vernix appears to have promise as a clinically effective therapeutic agent. Application of vernix to clinical use, however, has been limited by its physical properties. While vernix in utero is a tractable semi-solid, vernix ex utero is a nonhomogeneous intractable compound with a consistency comparable to cheese or hardened cake frosting. Vernix is not completely soluble in conventional solvents such as absolute ethanol, 95% ethanol, 2-propanol, and combinations of chloroform and methanol. Thus, controlled and uniform administration of vernix to a surface is difficult. While it has been reported that the surfactant polysorbate 80 (Tween 80) may solubilize vernix, Tween 80 is toxic to living cells and therefore cannot be used clinically. While there have been isolated reports of vernix directly scraped from a newborn baby for smearing over wounds (SU Patent No. 1718947A) or in an artificial lipid composition for use as a cosmetic moisturizer (U.S. Pat. No. 5,631,012), vernix in a therapeutic or prophylactic composition has not yet been reported.

While the barrier function and skin growth and maturational properties of vernix render it clinically useful to treat a variety of acute and chronic conditions, its physical properties have heretofore prevented its controlled administration in a clinical environment for therapeutic or prophylactic use. A need thus exists for a clinically useful vernix formulation.

SUMMARY OF THE INVENTION

This invention is directed to a composition comprising a normally intractable composition approximating vernix and a dispersing agent to render the vernix composition tractable. The composition may be a natural or synthetic vernix composition of about a 10% lipid fraction, about a 10% protein fraction, and about an 80% water fraction. The composition may have a skin curative or protectant effect and may be a film that is either freestanding or supported on a physiologically acceptable substrate. The substrate may be permeable and may include, for example, a diaper, a wound dressing, or a feminine hygiene product.

This invention is also directed to a method of enhancing growth and maturation of an epithelial layer of cells by applying a nontoxic film consisting essentially of vernix with a thickness of about 10 μm to about 500 μm to cover the epithelial cell layer and maintaining the film on the cell layer under growth enhancing conditions until a mature epithelial cell layer is obtained. The film may be applied to epithelial cells, and particularly may be applied to epidermal cells. The film may be applied to cells growing either in vivo or in vitro, and may be applied either directly to the cells or supported on a substrate.

This invention is further directed to a method of producing a nontoxic vernix film by dispersing vernix in a biocompatible liquid to form a dispersion containing vernix in a film-forming amount and applying the dispersion to a physiologically acceptable substrate. The biocompatable liquid may be, for example, dimethylsulfoxide (DMSO) or an amniotic fluid composition. The amniotic fluid composition may include lecithin or other phospholipids, bile salts, urea, growth factors, pulmonary surfactant proteins, and combinations thereof. A preferred dispersion comprises vernix in the range of about $5\%^{w/v}$ to about $20\%^{w/v}$ in about 100% DMSO with DMSO removed after being applied to the substrate.

The invention is still further directed to a skin-contacting product comprising a nontoxic vernix composition. The skin contacting product may be supported on a permeable substrate such as, for example, a diaper, a wound dressing, or a feminine hygiene product.

The invention is still further directed to a nontoxic fluid having a composition approximating vernix with the composition dispersed in a physiologically acceptable liquid for treating a layer of epithelial cells.

The invention is additionally directed to a method of preparing a nontoxic fluid consisting essentially of vernix and dispersing a therapeutically effective amount of vernix in a physiologically acceptable liquid. The biocompatible liquid may be, for example, DMSO or an amniotic fluid composition. The amniotic fluid composition may include lecithin and other phospholipids, bile salts, urea, growth factors, pulmonary surfactant proteins, and combinations thereof. A preferred dispersion comprises vernix in the range of about $5\%^{w/v}$ to about $20\%^{w/v}$ in about 100% DMSO with DMSO removed after being applied to the substrate.

The invention is also directed to a medical device comprising a normally intractable composition approximating vernix and a dispersing agent to render the composition tractable.

The invention is finally directed to a method of treating skin by applying a nontoxic film, consisting essentially of vernix in a film forming amount and having with a thickness of about 10 μm to about 500 μm, to a layer of epithelial cells to provide a skin curative and/or a skin protectant effect, and maintaining the film on the layer of cells under growth enhancing conditions until a mature epithelial layer of skin is obtained.

These and other methods and compositions will be apparent in light of the following detailed description and example.

DETAILED DESCRIPTION OF THE PREFERRED EMBODIMENT

A therapeutic agent or drug is defined as one that is used to treat a preexisting or impending condition or to affect a structure and/or function of the body. The treatment may be prophylactic, curative, protective, maturation enhancing or combinations of these. In contrast to a therapeutic agent, a cosmetic agent is defined as one that brings about an improved appearance but with no mandatory claims to efficacy.

Vernix compositions may be natural or synthetic. Natural vernix was obtained from a newborn infant at the time of delivery. Vernix comprises about a 10% lipid fraction by weight, about a 10% protein fraction by weight, and about an 80% volatile fraction by weight. As previously described, the lipid fraction has been reported to comprise lecithin and other phospholipids, squalene, waxes, wax esters, sterol esters, diol esters, triglycerides, free sterols and four classes of fatty acids ranging in chain length from $C_{12}$ to $C_{26}$ (straight chain saturated, straight chain unsaturated, branched chain saturated, and branched chain unsaturated). The lipid fraction may contain, with the relative percentages indicated, squalene (9%), aliphatic waxes (12%), sterol esters (33%), diesters (7%), triglycerides (26%), free sterols (9%), and other lipids (4%). The fatty acids within the aliphatic waxes may be branched and the branched fatty acids may be methylated. The protein fraction consists of epidermally derived proteins, primarily keratin and filaggrin. The protein fraction also contains trace amounts in the range of about micromolar to millimolar concentrations of regulatory proteins such as epidermal growth factor, and trace amounts of about nanomolar to micromolar concentrations of surfactant protein such as Surfactant A and Surfactant B. The volatile fraction is primarily water. The rate of evaporation of volatile components is relatively slow, presumably due to increased energy requirements for the dissociation of hydrogen bonds to change water from the liquid to the gaseous state. Vernix is an odorless material, again indicating the absence of volatile carbon or nitrogen containing compounds.

Synthetic vernix may be produced by mixing one part of natural vernix, removed from the infant at the time of delivery, with any of the following components in the proportions indicated: either about 0.005 to about 0.05 parts phospholipid, or trace amounts of about nanomolar to micromolar concentrations of pulmonary surfactant proteins such as Surfactant A and/or Surfactant B, or 5 parts dimethylsulfoxide (DMSO), or 1 part amniotic fluid, or combinations of the above. Alternatively, synthetic vernix may also be produced by combining lipids to comprise about a 10% fraction of the entire volume, proteins to comprise about a 10% fraction of the entire volume, and water to comprise the remaining about 80% of the entire volume. The following lipid components are combined in the relative percentages indicated: squalene (9%), aliphatic waxes (12%), sterol esters (33%), diesters (7%), triglycerides (26%), free sterols (9%), and other lipids (4%). The fatty acids within the waxes may be branched and the branched fatty acids may be methylated. The protein components, combined to constitute about a 10% fraction, are epidermally derived proteins, primarily keratin and filaggrin, with trace amounts of about micromolar to millimolar concentrations of regulatory proteins such as epidermal growth factor, and trace amounts of about nanomolar to micromolar concentrations of surfactant protein such as Surfactant A and Surfactant B.

Either natural or synthetic vernix must be rendered tractable and dispersible. A vernix dispersion, wherein vernix may not be in a true solution but may be in a number of different states, includes a suspension, a solid, or a semi-solid. In one embodiment, natural vernix in amounts sufficient to yield concentrations of $5\%^{w/v}$, $10\%^{w/v}$ or $20\%^{w/v}$, was added to either 50% or 100% dimethylsulfoxide (DMSO). The DMSO solvent was selected since it is an organic solvent that is routinely used in the preinoculation processing of cultured skin substitutes. Additionally DMSO is a well-known penetrant for the delivery of exogenous substances through the skin, indicating that DMSO is miscible with skin lipids and presumably is miscible with vernix. Finally, DMSO is a relatively volatile compound that is easily removed by evaporation. Mixtures of vernix and DMSO were sonicated at room temperature under a fume hood until the vernix was completely dispersed using a Cole-Parmer sonicator (Chicago, Ill.).

The extent of vernix dispersion was evaluated by monitoring its absorbance at 600 nm using a standard spectrophotometer. An increase in light absorbance indicated a more complete dispersion of vernix in the solvent. Conversely, an increase in light transmittance (decreased absorbance) indicated clumps of vernix in the solvent.

A mixture of $5\%^{w/v}$ vernix in 50% DMSO was evaluated. Visible clumps persisted even after the mixture was sonicated for several minutes. A mixture of $5\%^{w/v}$ vernix in 100% DMSO was evaluated. Increasing the DMSO concentration resulted in less clumping although a slurry, rather than a solution, was obtained. When the vernix concentration was increased to either $10\%^{w/v}$ or $20\%^{w/v}$ vernix in 100%

DMSO, the resulting dispersion was viscous but appeared void of clumps. Thus, 20%$^{w/v}$ vernix was deemed the preferred concentration for ease in handling. Agitation of the 20%$^{w/v}$ vernix in 100% DMSO resulted in a relatively uniform mixture.

The dispersion of 20%$^{w/v}$ vernix in 100% DMSO prepared as described above was formed into a film and applied to a biocompatible substrate as will be described below. The DMSO was evaporated by exposing the dispersion to a vacuum at room temperature (approximately 22° C.) for a period of time between 72 and 168 hours. In one embodiment, the solvent used was amniotic fluid, obtained from a newborn at the time of delivery. Amniotic fluid is known to contain factors such as pulmonary surfactant and phospholipid such as lecithin that may aid in vernix dispersion. In another embodiment, the solvent was the commercially pulmonary surfactant Survanta® (Abbott Laboratories, Inc., Columbus, Ohio). Combinations of these or other physiologically acceptable solvents may also be used.

In one embodiment, vernix dispersed in a biocompatible liquid was applied to a physiologically acceptable support structure in a liquid state to form a vernix film. A film is defined herein as an interfacial surface covering, in either a liquid or a solid state, with temperature-dependant properties. Film-forming techniques include but are not limited to spraying, extruding, blowing, pouring, evaporating, coating and painting. The vernix dispersion is presented as droplets which coalesce to form a film upon encountering the support.

In an alternate embodiment, a preformed vernix film is applied to a support. The physiologically acceptable support structure is one that can withstand sterilization, preferably by standard sterilization techniques known to one skilled in the art such as exposure to gamma radiation, autoclaving, and so on. The support structure is not limited to a particular composition or configuration and, depending upon its use, may or may not be sterilized and may take various forms. In one embodiment, the nontoxic vernix film is used to enhance skin cell maturation and may be applied to structures such as filters, membranes, beads, particles, and so on. Similarly, the support structure is not limited to a particular state of matter and may be a solid, a semi-solid, a gel and so on. In one embodiment, the support consists of a nylon monofilament interpositional surfacing material such as Interfaces pads (Winfield Laboratories, Inc., Dallas Tex.), Biobrane II® (Sterling Drug Inc., New York, N.Y.) or circular nylon filters of suitable porosity (Micron Separations Inc., Westboro, Mass.). Other support materials, however, could also be used to practice the invention.

In another embodiment, the nontoxic vernix film is used to promote wound healing and/or tissue repair and may be applied to various materials for placement either in direct contact or indirect contact with a skin site requiring treatment such as a wound, an abrasion, an ulcer, a burned area, a site of infection or irritation, a wart and so on. The support structure may be permeable to physical and/or chemical agents, and may take a variety of forms, depending upon its purpose and the extent of the area requiring dressing or treatment. The nontoxic vernix film may be applied to various synthetics such as thermoplastic films, blown films and breathable films, and various natural and synthetic fabric compositions such as woven, non-woven, spun, and stitched fabrics. The invention may be used in a variety of products, examples of which include wound dressings and coverings such as bandages, tapes, gauze, adhesive products applied for a short or long term to the skin, ostomy care products, hospital pads such as incontinent pads, absorbent pads, and examination pads, disposable and cloth diapers, and feminine hygiene products such as intralabial devices.

The vernix composition of the invention may be used therapeutically to promote skin growth, skin maturation, skin barrier formation, wound healing, skin flexibility, and tissue repair. The vernix composition of the invention may also be used as a skin protectant to promote skin barrier formation, skin moisture retention and skin flexibility.

The invention will be further appreciated in light of the following example.

EXAMPLE

A dispersion of 20%$^{w/v}$ vernix in 100% DMSO was prepared with sonication and agitation to form a homogenous mixture. Nine 2-mm holes were drilled into the bottom of each well of a standard six-well polystyrene tissue culture plate (Becton Dickinson Labware, Bedford, Mass.). A singular circular sterile nylon filter, 20 micron porosity, 25-mm diameter (Micron Separations Inc., Westboro, Mass.) was placed into each well. The nylon filters were coated with vernix by first pipetting one ml of the 20%$^{w/v}$ vernix solution onto the top of each filter. Excess liquid was then wicked out of the wells through the filters on the bottom of the plate using paper towels. Finally the remainder of the liquid was evaporated by placing the culture plate in a vacuum chamber for a period of between 72 and 168 hours. The vernix-coated filters were then sterilized by gamma-irradiation at 17kGy for use in skin culture.

Cultures of human skin were prepared by a standard technique inoculating human keratinocytes onto a fibroblast-impregnated collagen-glycosaminoglycan support. Cultures were assessed weekly for epidermal barrier formation by surface electrical capacitance using a dermal phase meter (Nova Technology Corporation, Gloucester, Mass.) and were sampled weekly for histology and mitochondrial enzyme activity. In addition, the conditioned culture medium was sampled daily for glucose and lactate levels. In one embodiment, three-day old cultured human skin substitutes were overlaid with the vernix coated nylon filter.

A nontoxic vernix film and methods of producing and using the film are thus disclosed. In addition, a vernix dispersion and methods of producing and using the dispersion are disclosed. The compositions and methods of the invention may be used for skin cell maturation and for wound healing and/or repair. Other variations or embodiments of the invention will also be apparent to one of ordinary skill in the art from the above description and example. For example, vernix may be formulated into a cream, such as a first aid cream, a cream for treating poison ivy or other forms of contact dermatitis, or a diaper rash cream. Thus, the forgoing embodiments are not to be construed as limiting the scope of this invention.

What is claimed is:

1. A composition comprising an intractable vernix composition and a dispersing agent to render said vernix composition tractable.

2. The composition of claim 1 wherein said vernix is selected from the group consisting of a natural vernix and a synthetic vernix.

3. The composition of claim 1 wherein said intractable vernix composition comprises about a 10% lipid fraction, about a 10% protein fraction, and about an 80% water fraction.

4. The composition of claim 1 having a skin curative effect.

5. The composition of claim 4 wherein the curative effect is selected from the group consisting of skin growth, skin maturation, wound healing, tissue repair, and combinations thereof.

6. The composition of claim 1 having a skin protectant effect.

7. The composition of claim 6 wherein the protectant effect is selected from the group consisting of a barrier function, a moisture retention function and combinations thereof.

8. The composition of claim 1 wherein the composition is film forming.

9. The composition of claim 1 wherein the composition is supported on a physiologically acceptable substrate.

10. The composition of claim 9 wherein the substrate is selected from the group consisting of a membrane, a film, a fabric, a wound dressing, an adhesive product, an ostomy care product, a hospital pad, an incontinent pad, an absorbent pad, an examination pad, a diaper, and a feminine hygiene product.

11. The composition of claim 9 wherein the substrate is permeable.

12. A method of enhancing growth and maturation of an epithelial layer of cells comprising applying a nontoxic film consisting essentially of vernix and having a thickness of about 10 $\mu$m to about 500 $\mu$m to cover the epithelial cell layer and maintaining the film on the cell layer under growth enhancing conditions until a mature epithelial cell layer is obtained.

13. The method of claim 12 wherein said vernix is selected from the group consisting of natural vernix and synthetic vernix.

14. The method of claim 12 wherein the cell layer is covered with the film supported on a physiologically acceptable substrate.

15. The method of claim 14 wherein the substrate is permeable.

16. The method of claim 12 wherein the film is applied to the layer of growing epithelial cells in vitro.

17. The method of claim 16 wherein the epithelial cells are epidermal cells.

18. The method of claim 12 wherein the film is applied to a layer of growing epithelial cells in vivo.

19. A method of producing a nontoxic vernix film comprising
dispersing vernix in a biocompatable liquid to form a dispersion containing vernix in a film-forming amount and applying said dispersion to a physiologically acceptable substrate.

20. The method of claim 19 wherein the biocompatable liquid is selected from the group consisting of dimethylsulfoxide (DMSO), an amniotic fluid composition, a pulmonary surfactant composition and combinations thereof.

21. The method of claim 20 wherein the amniotic fluid composition comprises lecithin, bile salts, urea, growth factors, a pulmonary surfactant protein and combinations thereof.

22. The method of claim 20 wherein the DMSO is about 100%$^{w/v}$ and contains vernix in the range of about 5%$^{w/v}$ to about 20%$^{w/v}$.

23. The method of claim 20 wherein the DMSO is removed before applying to the substrate.

24. The method of claim 19 wherein the substrate is a solid.

25. A skin contacting product comprising a nontoxic vernix composition and a substrate, said substrate selected from the group consisting of a membrane, a film, a fabric, a wound dressing, an adhesive product, an ostomy care product, a hospital pad, an incontinent pad, an absorbent pad, an examination pad, a diaper, and a feminine hygiene product.

26. The product of claim 25 wherein the substrate is permeable.

27. A nontoxic fluid having a vernix composition, said composition dispersed in a physiologically acceptable liquid for treatment of a layer of epithelial cells.

28. The fluid of claim 27 wherein said vernix is selected from the group consisting of a natural vernix and a synthetic vernix.

29. The fluid of claim 27 wherein said vernix composition comprises about a 10% lipid fraction, about a 10% protein fraction, and about an 80% water fraction.

30. The fluid of claim 29 having a skin curative effect.

31. The fluid of claim 30 wherein the curative effect is selected from the group consisting of skin growth, skin maturation, wound healing, tissue repair, and combinations thereof.

32. The fluid of claim 29 having a skin protectant effect.

33. The fluid of claim 32 wherein the protectant effect is selected from the group consisting of a barrier function a moisture retention function and combinations thereof.

34. A method of preparing a nontoxic fluid consisting essentially of vernix comprising dispersing a therapeutically effective amount of vernix in a biocompatable liquid.

35. The method of claim 34 wherein the biocompatable liquid is selected from the group consisting of dimethylsulfoxide (DMSO), an amniotic fluid composition, a pulmonary surfactant composition and combinations thereof.

36. The method of claim 35 wherein the amniotic fluid composition is selected from the group consisting of lecithin, bile salts, urea, growth factors, a pulmonary surfactant protein and combinations thereof.

37. The method of claim 35 wherein the DMSO is about 100%$^{w/v}$ and contains vernix in the range of about 5%$^{w/v}$ to about 20%$^{w/v}$.

38. The method of claim 34 wherein the vernix is first dispersed in DMSO followed by removal of DMSO.

39. A medical device comprising an intractable vernix composition and a dispersing agent to render said composition tractable.

40. The device of claim 39 wherein the vernix is selected from the group consisting of a natural vernix and a synthetic vernix.

41. The device of claim 39 wherein said intractable vernix composition comprises about a 10% lipid fraction, about a 10% protein fraction, and about an 80% water fraction.

42. The device of claim 39 having a skin curative effect.

43. The device of claim 39 having a skin protectant effect.

44. The device of claim 39 supported on a physiologically acceptable substrate.

45. The device of claim 44 wherein the substrate is selected from the group consisting of a membrane, a film, a fabric, a wound dressing, an adhesive product, an ostomy care product, a hospital pad, an incontinent pad, an absorbent pad, an examination pad, a diaper, and a feminine hygiene product.

46. The device of claim 45 wherein the substrate is permeable.

47. A method of treating skin comprising
applying a nontoxic film having a thickness of about 10 $\mu$m to about 500 $\mu$m and consisting essentially of vernix in a film-forming amount to a layer of epithelial cells to provide a skin treating effect, said effect selected from the group consisting of a curative effect, a protectant effect and combinations thereof; and maintaining said film on said layer of cells under growth enhancing conditions until a mature epithelial layer of skin is obtained.

48. The method of claim 47 wherein the film is applied to a physiologically acceptable support and said support is applied to said cells.

49. The method of claim 47 wherein the support is permeable.

50. The method of claim 47 wherein the support is selected from the group consisting of a membrane, a film, a fabric, a wound dressing, an adhesive product, an ostomy care product, a hospital pad, an incontinent pad, an absorbent pad, an examination pad, a diaper, and a feminine hygiene product.

51. The method of claim 47 wherein the film is applied to a layer of epithelial cells that are epidermal cells.

* * * * *